United States Patent [19]

Jandourek

[11] 4,240,832
[45] Dec. 23, 1980

[54] DENTAL PULP CAPPING AND CAVITY LINING COMPOSITION AND PREPARATIVE METHOD

[75] Inventor: Emil Jandourek, Livonia, Mich.
[73] Assignee: Sybron Corporation, Rochester, N.Y.
[21] Appl. No.: 11,389
[22] Filed: Feb. 12, 1979
[51] Int. Cl.³ .............................................. C09K 3/00
[52] U.S. Cl. ........................................................ 106/35
[58] Field of Search ........................ 106/35; 528/148; 260/38

[56] References Cited

U.S. PATENT DOCUMENTS

| | | | |
|---|---|---|---|
| 1,318,254 | 10/1919 | Andresen | 106/35 |
| 2,413,294 | 12/1946 | Curtis | 106/35 |
| 2,516,438 | 7/1950 | Wheeler | 106/35 |
| 3,047,408 | 7/1962 | Dougherty | 106/35 |
| 4,080,212 | 3/1978 | Takahashi | 106/35 |

*Primary Examiner*—Theodore Morris
*Attorney, Agent, or Firm*—Theodore B. Roessel; Owen D. Marjama

[57] ABSTRACT

This invention discloses an improved dental pulp capping and cavity lining composition which is successful in capping and preserving the vitality of moderately inflammed, as well as normal, healthy dental pulps and also serves as an acid resistant, protective cavity liner. This composition is prepared by reacting suitable phenolic derivatives with formaldehyde or its polymer, under carefully controlled conditions, to form a low molecular weight polymer condensate, which is first purified and then compounded into a two-paste composition of optimized utility. In use, one paste portion, containing the condensate, reacts with the other paste portion, containing calcium hydroxide, to yield after mixing a solid protective layer of set material, which facilitates healing of the pulp and formation of secondary dentin.

13 Claims, No Drawings

DENTAL PULP CAPPING AND CAVITY LINING COMPOSITION AND PREPARATIVE METHOD

BACKGROUND OF THE INVENTION

This invention relates to an improved dental pulp capping and cavity lining composition and its method of preparation. The beneficial effect of calcium hydroxide on tooth pulp and secondary dentine formation has been well known in dentistry for many decades. The original calcium hydroxide suspensions were later mostly replaced by hard setting calcium hydroxide formulations.

Three prior art disclosures for which United States Patents were subsequently granted have special relevance to the present invention. U.S. Pat. No. 2,516,438 advocates that a mixture of excess calcium hydroxide and eugenol be used as pulp capping material. This was prior to the advent of polymerizable, acrylic functional, dental restorative materials, the setting of which is unfortunately inhibited by compositions containing eugenol, all of which contain some residual free eugenol even after many years. It is reported in the Science of Dental Materials (R. W. Phillips) 1973, Chapter 7, page 93, that as much as 5 percent free eugenol, from an original eugenol content of 16.4 percent, may be present in a zinc oxide and eugenol mixture, even ten years after mixing, and a similar finding would be expected in the case of calcium hydroxide and eugenol.

Since the presence of excess available free calcium hydroxide has been found beneficial in the stimulation of reparative secondary dentin formation over exposed dental pulps, U.S. Pat. No. 3,047,400 advocated the continued use of calcium hydroxide, but now reacted with non-eugenol phenolic derivative, to achieve compatibility with the newly introduced, unfilled acrylic restorative materials.

After 1965, filled acrylic functional resin based composite restoratives were introduced and rapidly gained wide acceptance. Concurrent with this development the use of the acid-etched enamel bonding technique also gained very wide acceptance, creating a need for pulp capping and cavity lining materials to be acid resistant. U.S. Pat. No. 4,080,212, places major emphasis on the prime objective stated as "the prevention of discoloration", even foregoing all the inherent advantages of a two paste system in order to achieve this objective.

Accordingly, it is an object of this invention to provide a dental pulp capping composition which when placed over moderately inflamed dental pulp will reduce inflammation and induce dentinal bridge formation thus increasing the probability of pulp healing.

It is also an object of this invention to provide a dental cement composition capable of fast curing in an oral environment and having high crushing strength to resist amalgam condensation pressure.

It is another object of this invention to provide a pulp capping and cavity lining material which is resistant to the type and concentration of acids used for etching tooth enamel and which also exhibits complete compatibility with composite restorative materials.

It is a further object of the present invention to provide a novel capping and cavity liner material in the form of a two paste system.

SUMMARY OF THE INVENTION

The above objects and other advantages are achieved based upon the use of condensates of suitable alkyl salicylates with suitable aldehydes, reduced in viscosity by blending with a further quantity of a similar alkyl salicylate, and reacted with calcium hydroxide or calcium oxide, in stoichiometric excess over the resin condensate blend. The resulting product comprises a rigid semipermeable, layer of a calcium phenolate complex, containing excess available calcium hydroxide dispersed therein.

DETAILED DESCRIPTION OF THE INVENTION

The resin condensates found most useful in accordance with this invention are prepared by the condensation of an alkyl salicylate with formaldehyde or its polymer. These resin condensates are prepared by the methods used for many years for the preparation of conventional phenol formaldehyde resins and described in numerous chemical literature references.

When combined with calcium hydroxide the reaction time of the resin condensate increases with an increase in size of the alkyl groups. At the same time the compressive strength decreases with an increase in the size of the alkyl groups. Satisfactory results were obtained with a range of alkyl groups having from one to six carbon atoms, that is up to and including hexyl salicylate.

Acetaldehyde, as well as formaldehyde, was found suitable for synthesis of the resin condensate. The chosen resin condensate is then blended with a further quantity of the preferred alkyl salicylates to obtain a blend of suitable viscosity for the preparation of a paste. This alkyl salicylate acts as a reactive diluent and thus ensures that adequate physical properties are obtained, following the reaction with the calcium hydroxide, after mixing.

This resin condensate blend is made into a radiopaque paste by mixing with one or more inert fillers, at least one of which should be radiopaque, and all of which should be essentially insoluble in water.

Since radiopacity is approximately proportional to the square root of the atomic weights of the constituent elements, insoluble barium compounds, particularly finely divided barium sulfate, are preferred radiopaque fillers which may be beneficially augmented with other inert, insoluble fillers, such as titanium oxide, submicron silica, iron oxide pigments, etc.

The second paste, containing calcium oxide or hydroxide extended with zinc oxide, utilizes an inert liquid vehicle as the matrix liquid. In order to ensure desirable physical properties, it is essential that the calcium hydroxide-salicylate condensate reaction of the present invention be formulated using a stoichiometric excess of calcium hydroxide. Furthermore, this unreacted excess of calcium hydroxide is dispersed throughout the set material and is a source of partially leachable free calcium hydroxide which is available to assist in the stimulation of secondary dentine formation. Additionally, the set and hardened layer of material, which is a complex calcium polysalicylate, will resist penetration or disintegration by acid etchants used in dentistry, and the presence of excess dispersed calcium hydroxide will neutralize any such acid inadvertently coming into contact with the pulp capping material, thus protecting the pulp from accidental acid percolation.

The ranges of composition which have been found suitable for synthesis of the resin condensate and the catalyst paste formulated from it are as follows:

Resin Condensate

An aldehyde to salicylate ratio of about 0.5 to 1.0 moles of aldehyde per mole of salicylate, with the preferred ratio being about 0.55 to 0.75 moles of aldehyde per mole of salicylate.

Resin Condensate/Alkyl Salicylate Blend

(Catalyst Paste Matrix Liquid)

A resin condensate to alkyl salicylate ratio of between about 40 and 80 parts by weight of resin condensate to between about 60 and 20 parts by weight of alkyl salicylates, with the preferred ratio being between about 65 and 80 parts by weight of resin condensate to between about 35 and 20 parts by weight of alkyl salicylate.

Catalyst Paste Matrix Liquid to Filler Ratio

A catalyst paste matrix liquid to filler ratio of between about 30 and 70 parts by weight of matrix liquid to between about 70 and 30 parts by weight of filler, with the preferred ratio being between about 40 and 60 parts by weight of matrix liquid to between about 50 and 40 parts by weight of filler.

The ranges of composition which have been found suitable for formulation of the base paste can be varied within fairly wide limits, but in order to preserve adequate physical properties consistent with good paste flow, the powder to liquid ratio of the paste should be optimized. In addition, in order to ensure availability of an adequate excess of free calcium hydroxide, a substantial stoichiometric excess of the latter over the resin condensate should always be utilized.

The consistency of the mixed material is a free-flowing, creamy, paste which can be conveniently placed, without pressure, over exposed pulp tissue or a prepared dentine surface in a tooth cavity, and when in contact with the tooth structure warms quickly to body temperature, decreasing in viscosity and spreading easily. The mixed material adheres to the moist dentine surface and functions well as a protective barrier.

A preferred example of a two-paste formulation suitable for use in the present invention is listed below:

| Catalyst Paste | Parts by Weight |
| --- | --- |
| Resin condensate | 38.0 |
| Methyl salicylate | 12.0 |
| Barium Sulfate | 37.9 |
| Titanium Dioxide | 10.0 |
| Aerosil R972 silica (a tradename of Degussa Corp., Teterboro, New Jersey) | 2.0 |
| Mapico 3100 pigment (a tradename for iron oxide pigments sold by Citco Pigment Division, New York, New York) | 0.1 |
|  | 100.0 |
| Base Paste | Parts by Weight |
| Calcium Hydroxide | 51.3 |
| Zinc Oxide | 13.75 |
| Zinc Stearate | 0.25 |
| Ethyl toluenesulfonamide | 34.00 |
| Distilled water | 0.7 |
|  | 100.0 |

When required for use, suitable quantites of catalyst and base paste are mixed in equal proportions. The setting time of the material is controlled by the addition of a small amount of water, providing work time flexibility, so that formulations can be prepared which are usable at high ambient temperatures and humidities, yet will set rapidly when applied to the base of a cavity preparation. The following examples serve to illustrate the methods of preparation of the resin condensate, catalyst paste and base paste:

EXAMPLE I

A calcium hydroxide containing base paste of the following formulation was prepared:

|  | Parts by Weight |
| --- | --- |
| Calcium Hydroxide USP | 53.5 |
| Zinc Oxide | 9.7 |
| Zinc Stearate | 0.3 |
| Ethyl Toluenesulfonamide | 36.5 |
|  | 100.0 |

This formulation is disclosed in Example V of U.S. Pat. No. 3,047,408 and is later used to compare the composition of the present invention with a commercially available material manufactured according to the U.S. Pat. No. 3,047,408.

EXAMPLE II

Methyl salicylate-formaldehyde resin condensate was prepared according to the following procedure: 22.8 parts of methyl salicylate, 3 parts of paraformaldehyde, 3 parts of glacial acetic acid and 0.6 parts of zinc chloride were placed in a boiling flask fitted with reflux condenser, thermometer, stirrer and heating mantle. The mixture was heated slowly with stirring until gentle reflux conditions were reached and maintained for approximately 48 hours until the last traces of paraformaldehyde sublimation disappeared.

After the condensation is completed the resin is purified by multiple washings with deionized water to remove the water soluble materials from the condensate. The resin was then stripped of all volatile material under vacuum, with the temperature being finally raised to 250° C.

The resin condensate remained as a light brown viscous liquid, which when cooled below 60° C. formed a solid amorphous resinous mass.

EXAMPLE III

Six catalyst pastes were prepared using various phenolic derivatives, including mono and disalicylate esters, and a 65% solution of the resin condensate from Example II in methyl salicylate, to the following general formula:

|  | Parts by Weight |
| --- | --- |
| Phenolic derivative | 50.0 |
| Barium sulfate | 35.0 |
| Titanium Dioxide | 15.0 |
|  | 100.0 |

The ingredients were mixed together and homogenized on a three roll mill. Equal parts of each catalyst paste were mixed in turn with an equal volume of the base paste from Example I and the setting times measured with the following results:

| Phenolic Derivative | Setting Time |
| --- | --- |
| Methyl salicylate USP | less than 1 min |

-continued

| Phenolic Derivative | Setting Time |
| --- | --- |
| Ethyl salicylate | less than 1 min |
| Isobutyl salicylate | less than 1 min |
| Hexyl salicylate | less than 1 min |
| 1,3 butylene Glycol disalicylate | less than 5 mins |
| 65/35 methyl salicylate/paraformaldehyde condensate in methyl salicylate (resin of the present invention) | more than 10 mins |

The setting time of all of the above formulations based on monoalkyl salicylates is too fast to have an practical use in denistry and therefore only the last two formulations were evaluated for compressive strength. A trace of water was used to accelerate materials prepared according to the present invention. The following results were obtained:

|  | 1,3 Butylene Glycol Disalicylate | 65/35 Methyl Salicylate Paraformaldehyde condensate in Methyl Salicylate |
| --- | --- | --- |
| Setting time at 23° C. | 3 min 50 sec. | 5 min. 0 sec |
| 7 mins compressive strength 37° C. 100% RH | 1014 psi | 2211 psi |
| Compressive strength 15 mins 37° C. 100% RH | 1436 psi | 3914 psi |

EXAMPLE IV

The same method as described in Example II was used for preparation of the following resin condensates:
Methyl salicylate/acetaldehyde resin condensate
Isobutyl salicylate/formaldehyde resin condensate
Isobutyl salicylate/acetaldehyde resin condensate
Hexyl salicylate/acetaldehyde resin condensate
Hexyl salicylate/formaldehyde resin condensate
Ethyl salicylate/acetaldehyde resin condensate
Ethyl salicylate/formaldehyde resin condensate It was observed that the necessary reaction time seemed to increase with increasing size of the alkyl group of the salicylate ester, and also when acetaldehyde was substituted for paraformaldehyde. All of these resin condensates were tested, following dilution with various different monoalkyl salicylates, and their physical properties were similar, but with a trend towards lower compression strength with increasing size of the alkyl group of the salicylates ester.

EXAMPLE V

The acid resistance of the material manufactured according to the U.S. Pat. No. 3,047,408 was compared to the material of Example IV. Thin layers of both materials were spread on the glass slab and allowed to set for 1 minute at 37° C. and 100% relative humidity. One drop of 50% phosphoric acid was placed on each material and after 1 minute removed with an excess of water. The commercially available material according to U.S. Pat. No. 3,047,408 showed a deep indentation where the acid was placed with porous structure at the bottom. The material according to the present invention only lost its luster without any detectable indentation even under magnification.

The above examples are not intended to limit the scope of the invention or the applications to which this invention may be directed. It is to be understood that although the invention has been described with specific reference to particular embodiments thereof, it is not to be so limited, since changes and alterations therein may be made which are within the full intended scope of this invention as defined by the appended claims.

I claim:

1. A dental composition which comprises calcium hydroxide and a condensate of an ester of salicylic acid and an aldehyde selected from the group consisting of acetaldehyde, formaldehyde and its oligomers, such as paraformaldehyde and metaformaldehyde or trioxane, and where the aldehyde to salicylate ratio is from about 0.5 to 1.0 moles of aldehyde per mole of salicylate, the calcium hydroxide being present in stoichiometric excess over said condensate, which reacts with it to form a hard, rigid mass, containing free calcium hydroxide dispersed therein.

2. A dental cement composition consisting essentially of calcium hydroxide and a condensate of an ester of salicylic acid and a selected aldehyde, said ester of salicylic acid being selected from a group consisting of alkyl and certain aryl salicylates, including the methyl, ethyl, propyl, isobutyl butyl hexyl and benzyl esters, while the said aldehyde may be selected from the group consisting of alkyl aldehydes including acetaldehyde, formaldehyde and its oligomers, such as paraformaldehyde and metaformaldehyde or trioxane.

3. A dental cement composition comprising calcium hydroxide and a condensate of an ester of salicylic acid and an aldehyde diluted to a suitable viscosity said aldehyde being selected from the group consisting of acetaldehyde, formaldehyde and its oligomers, such as paraformaldehyde and metaformaldehyde or trioxane with alkyl salicylates selected from the group consisting of alkyl and aryl salicylates including methyl, ethyl, propyl, isobutyl, butyl hexyl and benzyl esters, and where the aldehyde to salicylate ratio is from about 0.5 to 1.0 moles of aldehyde per mole of salicylate.

4. A dental cement composition consisting essentially of a first paste containing the reaction product of a salicylate ester and an aldehyde selected from the group consisting of acetaldehyde, formaldehyde and its oligomers, such as paraformaldehyde and metaformaldehyde or tioxane, diluted to suitable viscosity and mixed to a paste with certain fillers, at least one of which is radiopaque, and suitable pigments, and a second paste comprising calcium hydroxide, zinc oxide and zinc stearate, plus suitable liquid matrix, said calcium hydroxide being present in stoichiometric excess over said reaction product in the first past so that following admixture in equal proportions a hard rigid mass is formed.

5. A dental cement composition which comprises a first paste containing the condensate of about sixteen equivalents of methyl salicylate and about ten to thirteen equivalents of paraformaldehyde and a second paste comprising about 35 parts of mixed ortho and para isomers of N-ethyl, toluenesulfonamide, about 50 parts of calcium hydroxide, about 14 parts of zinc oxide and approximately one part of zinc stearate said calcium hydroxide being present in stoichiometric excess over said reaction product and reactable with it upon admixture to form a hard, rigid mass wherein the excess of free calcium hydroxide is continuously available for promotion of a secondary dentin growth.

6. A dental composition consisting essentially of a mixture of about 20% of the condensate of methyl salicylates and paraformaldehyde, plus about 5% methyl salicylate diluent and about 60% of a blend of solids consisting of calcium hydroxide, titanium dioxide, barium sulfate and zinc oxide, plus pigments and sub micron silaceous thickener, and about 15% mixed ortho and para isomers of n-ethyl toluenesulfonamide.

7. A composition as defined in claim 1 which further contains at least one inert powdered filler.

8. A composition as defined in claim 1, containing an inert powdered filler selected from the group consisting of silica, titanium dioxide, barium sulfate and mixtures thereof or any other inert combination of suitable radiolucent or radiopaque fillers.

9. A composition as defined in claim 1 which contains a plasticizer miscible with the particular condensate of an ester of salicylic acid and the selected aldehyde which is employed, said plasticizer not entering into the reaction between said condensate and calcium hydroxide and consisting of ethyltoluenesulfonamide or other suitable liquids.

10. A composition as defined in claim 5 wherein the resin condensate is selected from an aldehyde to salicylate ratio of about 0.5 to 1.0 moles of aldehyde per mole of salicylate.

11. A composition as defined in claim 5 wherein the resin condensate is selected from an aldehyde to salicylate ratio of about 0.7 to 0.9 moles of aldehyde per mole of salicylate.

12. A composition as defined in claim 6 wherein the resin condensate to alkyl salicylate ratio is 40 to 80 parts resin condensate to 60 to 20 parts alkyl salicylate by weight.

13. A composition as defined in claim 6 wherein the solid to liquid ratio is 30 to 70 parts liquid to 70 to 30 parts solid by weight.

* * * * *